Sept. 15, 1964 R. KORDES Plant Pat. 2,445
ROSE PLANT
Filed Oct. 21, 1963
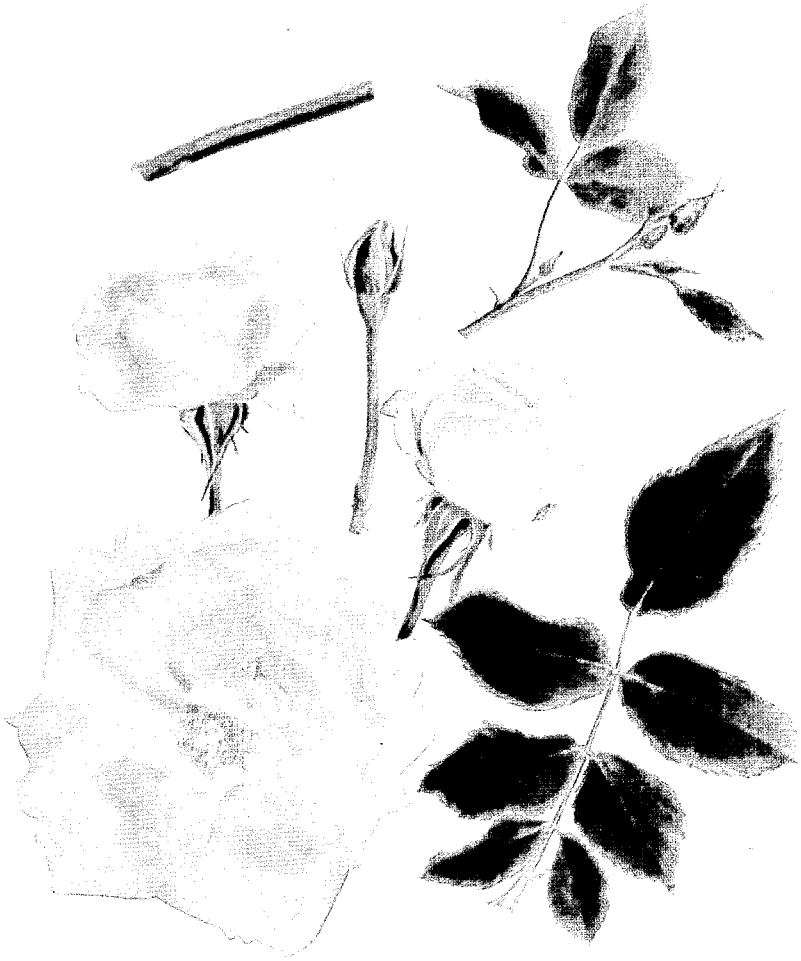
Inventor.
Reimer Kordes
By: Robb & Robb
Attorneys United States Patent Office Plant Pat. 2,445
Patented Sept. 15, 1964

2,445
ROSE PLANT

Reimer Kordes, Barmstedt, near Elmshorn, Germany, assignor to Jackson & Perkins Company, Newark, N.Y., a corporation of New York Filed Oct. 21, 1963, Ser. No. 317,855
1 Claim. (Cl. Plt.—28)

The present invention relates to a new and distinct variety of rose plant of the floribunda class, which was originated by me by crossing the floribunda variety known as "Korona" (unpatented) with the floribunda variety known as "Spartan" (U.S. Plant Patent No. 1,357).

The primary objective of this breeding was to produce a new rose variety in which the flower color of the parent variety "Korona" is combined with the plant and flower habits of the parent variety "Spartan." This objective was fully achieved, as evidenced by the following unique combination of characteristics which are outstanding in the new variety and distinguish it from its parents, as well as from all other varieties of which I am aware:

(1) A healthy, vigorous and free habit of plant growth, equal to that of the variety "Spartan";

(2) A very free blooming habit;

(3) A distinctive and attractive rich glowing Scarlet Red general color tonality of the flowers which are very resistant to fading due to sun or rain, with consequent good color retention to the end of the blooms; and (4) Good lasting quality of the flowers both on the bush and as cut flowers.

Asexual reproduction of the new variety by budding, as performed at Newark, New York, U.S.A., and also at Pleasanton, California, U.S.A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Korona."
*Pollen parent.*—"Spartan."
Classification:
*Botanic.*—Floribunda.
*Commercial.*—Floribunda.

*Flower*

(Observations made from specimens grown outdoors at Newark, New York, U.S.A., in the early morning during the latter part of the month of August.)

Blooming habit: Recurrent—continuous.
Bud:
*Size.*—Large.
*Form.*—Ovoid; is not affected by wet or hot weather.
*Color.*—When sepals first divide—Eugenia Red, Plate 13. When petals begin to unfurl—Spectrum Red, Plate 1. When half-blown: inside of petals—Scarlet Red, Plate 1, very lightly overcast with Scarlet, Plate 1; reverse of petals—Spectrum Red, Plate 1, lightly overcast with Scarlet, Plate 1.
*Sepals.*—Slightly branched; curl back when petals begin to unfurl. Color: inside—Rainette Green, Plate 31, lightly overcast with Spinel Red, Plate 26; outside—Chromium Green, Plate 32.

*Calyx.*—Color—Chromium Green, Plate 32. Shape — pear. Size — long. Aspect — smooth. Odor when rubbed—none.
*Peduncle.* — Length — medium. Aspect — smooth. Strength — erect; heavy. Color — Courge green, Plate 17, overcast with Eugenia Red, Plate 13.
*Opening.*—Opens up well; is not affected by adverse weather conditions.
Bloom:
*Size.*—Large. Average size when fully expanded—from 4 inches to 4½ inches.
*Borne.*—Both singly and several together in irregular clusters.
*Stems.*—Medium length; strong.
*Form (when first open).*—High-centered. Permanence—retains its form to the end, but outer petals become lightly reflexed.
*Petalage.*—Double (full but open center). Number of petals under normal conditions—from 40 to 45.
*Color.*—Center of flower—Scarlet Red, Plate 1. Outer petals—Scarlet Red, Plate 1, overcast with Scarlet, Plate 1. Base of petals (aiglet)—Barium Yellow, Plate 16. Inside of petals—Scarlet Red, Plate 1, lightly overcast with Scarlet, Plate 1. Reverse of petals—Scarlet, Plate 1, very lightly overcast with Scarlet Red, Plate 1. General tonality from a distance—Scarlet Red, Plate 1, lightly overcast with Scarlet, Plate 1.
*Discoloration.*—Non-fading. General tonality at end of first day—Scarlet Red, Plate 1. Second day—Scarlet Red, Plate 1, lightly overcast with Scarlet, Plate 1. Third day—Scarlet Red, Plate 1, lightly overcast with Scarlet, Plate 1.
Petals:
*Texture.*—Leathery; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; large.
*Persistence.*—Drop off cleanly.
*Fragrance.*—Slight. nature—tea (average hybrid tea scent).
*Lasting quality.*—On the plant—long. As cut flower—long.

*Genital Organs*

Stamens, anthers: Medium side; many; regularly arranged around styles. Color—Antimony Yellow, Plate 15.
Stamens, filaments (threads): Medium length. Color—Massicot Yellow, Plate 16.
Pollen: Color—Light Buff, Plate 15.
Styles: Bunched; uneven length; medium length; thin.
Stigmas: Color—Naphthalene Yellow, Plate 16.
Ovaries: All enclosed in calyx.
Hips: None.
Seeds: None.

*Plant*

Form: Bush.
Growth: Vigorous; upright; free-growing; healthy.
Foliage: Compound of 5–7 leaflets.
*Size.*—Medium.
*Quantity.*—Normal.
*Color.*—New foliage: upper side—Cerro Green, Plate 5, lightly overcast with Oxblood Red, Plate 1; under side—Carmine, Plate 1. Old foliage: upper side—Empire Green, Plate 32; under side—Light Cress Green, Plate 31.
*Shape.*—Oval pointed.

*Texture.*—Upper side—Leathery; glossy. Under side—smooth.

*Ribs and veins.*—Ordinary.

*Edge.*—Serrated (saw-toothed).

*Serration.*—Both double and single; small.

*Leaf stem.*—Color—Rainette Green, Plate 31. Under side—prickly.

*Stipules.*—Medium length; slightly bearded.

Wood:

*New wood.*—Color—Light Cress Green, Plate 31, lightly overcast with Pompeian Red, Plate 13. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; hooked downward. Color (when young)—Begonia Rose, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of a healthy, vigorous and free plant growth equal to that of the variety "Spartan" (U.S. Plant Patent No. 1,357), a very free blooming habit, a distinctive and attractive rich, glowing, Scarlet Red general color tonality of the flowers which are very resistant to fading due to sun or rain, with consequent good color retention throughout the life of the flowers, and good lasting qualities of the flowers both on the bush and as cut flowers.

No references cited.